(12) United States Patent
Jung et al.

(10) Patent No.: US 7,848,890 B2
(45) Date of Patent: Dec. 7, 2010

(54) METHOD AND SYSTEM FOR PREDICTING GENE PATHWAY USING GENE EXPRESSION PATTERN DATA AND PROTEIN INTERACTION DATA

(75) Inventors: Ho Youl Jung, Seoul (KR); Mi Young Shin, Daejeon (KR); Sun Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1222 days.

(21) Appl. No.: 11/297,008

(22) Filed: Dec. 7, 2005

(65) Prior Publication Data

US 2006/0122792 A1     Jun. 8, 2006

(30) Foreign Application Priority Data

Dec. 8, 2004   (KR) .................... 10-2004-0102913
Jul. 28, 2005   (KR) .................... 10-2005-0068784

(51) Int. Cl.
*G01N 33/48*   (2006.01)

(52) U.S. Cl. ........................................... 702/19
(58) Field of Classification Search .................... 702/19
See application file for complete search history.

(56) References Cited

FOREIGN PATENT DOCUMENTS

KR   1020030071225 A   9/2003

OTHER PUBLICATIONS

E. Segal et al., "Discovering molecular pathways from protein interaction and gene expression data", Bioinformatics 19(1), © Oxford University Press 2003, vol. 19 Suppl 1, 2003, pp. 1264-1272, DOI: 10. 1093/bioinformatics/btg 1037.

N. Przulj et al., "Functional topology in a network of protein interactions", Bioinformatics 20(3), © Oxford University Press 2004, vol. 20 No. 3, 2004, pp. 340-348, DOI: 10. 1093/bioinformatics/btg 415.

*Primary Examiner*—Jerry Lin
(74) *Attorney, Agent, or Firm*—Blakely, Sokoloff, Taylor & Zafman LLP

(57) ABSTRACT

Provided are a method and system for predicting pathways of genes that serve the same biological purpose using gene expression pattern data and protein interaction data. The method of predicting a gene pathway includes: a first step of generating partial pathways from gene expression pattern data by using a pathway extraction algorithm, and matching the partial pathways to express them as a graph; a second step of generating partial pathways from protein interaction data by using a pathway extraction algorithm, and matching the partial pathways to express them as a graph; and a third step of combining a graph made in the first step and a graph made in the second step by using a graph matching algorithm to make a combined graph.

6 Claims, 5 Drawing Sheets

METHOD AND SYSTEM FOR PREDICTING GENE PATHWAY USING GENE EXPRESSION PATTERN DATA AND PROTEIN INTERACTION DATA

CROSS-REFERENCE TO RELATED APPLICATION

This application claims priority to and the benefit of Korean Patent Application Nos. 2004-102913 filed on Dec. 8, 2004 and 2005-68784 filed on Jul. 28, 2005, the disclosure of which is incorporated herein by reference in its entirety.

BACKGROUND

1. Field of the Invention

The present invention relates to a method and system for predicting pathways (biological pathways) of genes that serve the same biological purpose, and more particularly, to a method and system for predicting pathways of genes that serve the same biological purpose using gene expression pattern data and protein-protein interaction (PPI) data.

2. Discussion of Related Art

When mechanism of development or pathway of a disease such as cancer is known, it is possible to cure the disease by treating genes on the pathway. However, it requires considerable time and cost to identify the pathways one by one through biological experiments.

It would be very helpful in finding cures for diseases if significant pathways could be predicted from data derived from experiments that can be performed on a large scale and do not require numerous trials.

Meanwhile, since a sequence of genes was identified by the human genome project, the study and analysis of the functions of genes, known as functional genomics, has attracted considerable attention. Functional genomics has developed remarkably thanks to DNA chips and protein interactions which facilitate large-scale experimentation. Such large-scale experimentation has helped to study and analyze groups or pathways of genes that have the same biological function and purpose rather than predict functions of individual genes.

Typically, a method of clustering a gene using an expression pattern of mRNA has been used, but it merely provides information translated by genes which express an identical function bound into one, and thus it is difficult to get information about relation between genes.

Accordingly, research into a way to derive more accurate information about genes is as active as ever.

For example, *"Discovering Molecular Pathways from Protein Interaction and Gene Expression Data"* by E. Segal, H. Wang & D. Koller, ISMB 2003, Jun. 29-Jul. 3, 2003, Bioinformatics Vol. 19(sup), pages i264-i272, July 2003, discloses a method for searching groups of genes on the same biological pathway from a large amount of gene expression data and PPI data. While this method yields more accurate results than the existing clustering method based on the MRNA expression pattern, like the gene clustering method, it is focused on discovering genes which have a possibility of being on the same pathway rather than obtaining information about relationships between individual genes.

*"Functional topology in a network of protein interactions"* by Natasa Przulj, Dennis A. Wigle & Igor Jurisica, Bioinformatics, volume 20, number 3, pages 340-348, 2004 (this article is hereby incorporated in the present invention by reference), discloses a method of searching for a biological pathway using PPI data. According to this article, the PPI data are expressed using an interaction graph, and a biological pathway is searched for using a similar shortest path algorithm in the graph. However, since there is not much actual PPI data, there is a limit to the number of pathways that can be obtained, and thus the results of this experimental method have low reliability.

While researching a solution to the foregoing problems that would enable more accurate prediction of a biological pathway of genes, the present inventors discovered that prediction of a biological pathway by using mRNA expression pattern data and PPI data obtained by the DNA chip method yields more accurate and reliable experimental results because two biological experimental results are combined to obtain high reliability and more information enables to generate more accurate results. This discovery led to the present invention.

SUMMARY OF THE INVENTION

The present invention is directed to a method of predicting biological pathways using gene expression pattern data and PPI data.

The present invention is also directed to a system for predicting biological pathways using gene expression pattern data and PPI data.

According to an aspect of the present invention, there is provided a method of predicting a gene pathway, comprising: a first step of generating partial pathways from the gene expression pattern data by using a pathway extraction algorithm, and matching partial pathways to express them as a graph; a second step of generating partial pathways from PPI data by using a pathway extraction algorithm, and matching the partial pathways to express them as a graph; and a third step of combining a graph obtained in the first step and a graph obtained in the second step by using a graph matching algorithm to make a combined graph.

The first step may comprise inputting the gene expression pattern data; generating a gene expression similarity graph from the gene expression pattern data by plotting each gene as a point, expressing gene expression pattern similarity as a distance between the points corresponding to the genes, and connecting the points if the distance between the two points is greater than a prescribed threshold; generating the partial pathways from the gene expression similarity graph by using a shortest path algorithm; and treating each of the generated partial pathways as a graph and expressing the partial pathways as a graph by using a graph matching algorithm.

The second step may comprise inputting the PPI data of genes; generating a PPI graph from the PPI data by plotting each gene as a point, expressing PPI similarity as a distance between the points corresponding to the genes, and connecting the points if the distance between the two points is greater than a prescribed threshold; generating biological partial pathways from the PPI graph by using a shortest path algorithm; and treating each of the generated partial pathways as a graph and expressing the partial pathways as a graph by using a graph matching algorithm.

The graph obtained in the first step and the graph obtained in the second step may be combined by an algorithm which determines the two graphs to be matched when the number of points that are regarded as matched between two graphs is greater than a prescribed threshold.

According to another aspect of the present invention, there is provided a system for predicting a biological pathway of a gene, comprising: a first database for storing gene expression pattern data obtained by a DNA chip method or a reaction experiment on specific chemicals; a second database for storing the PPI data of a gene whose expression pattern data is stored in the first database; and a pathway predicting unit comprising a shortest path extractor for generating partial pathways by using a shortest path algorithm from the gene expression data stored in the first database and the PPI data stored in the second database, and a partial pathway coupler for coupling the partial pathway generated from the gene expression data stored in the first database and the partial pathway generated from the PPI data stored in the second database.

BRIEF DESCRIPTION OF THE DRAWINGS

The above and other features and advantages of the present invention will become more apparent to those of ordinary skill in the art by describing in detail preferred exemplary embodiments thereof with reference to the attached drawings in which.

DETAILED DESCRIPTION OF EXEMPLARY EMBODIMENTS

Hereinafter, exemplary embodiments of the present invention will be described in detail. However, the present invention is not limited to the exemplary embodiments disclosed below and can be implemented in various modified forms. The exemplary embodiments are provided for complete disclosure of the present invention and to fully inform the scope of the present invention to those ordinarily skilled in the art.

Figure 1:
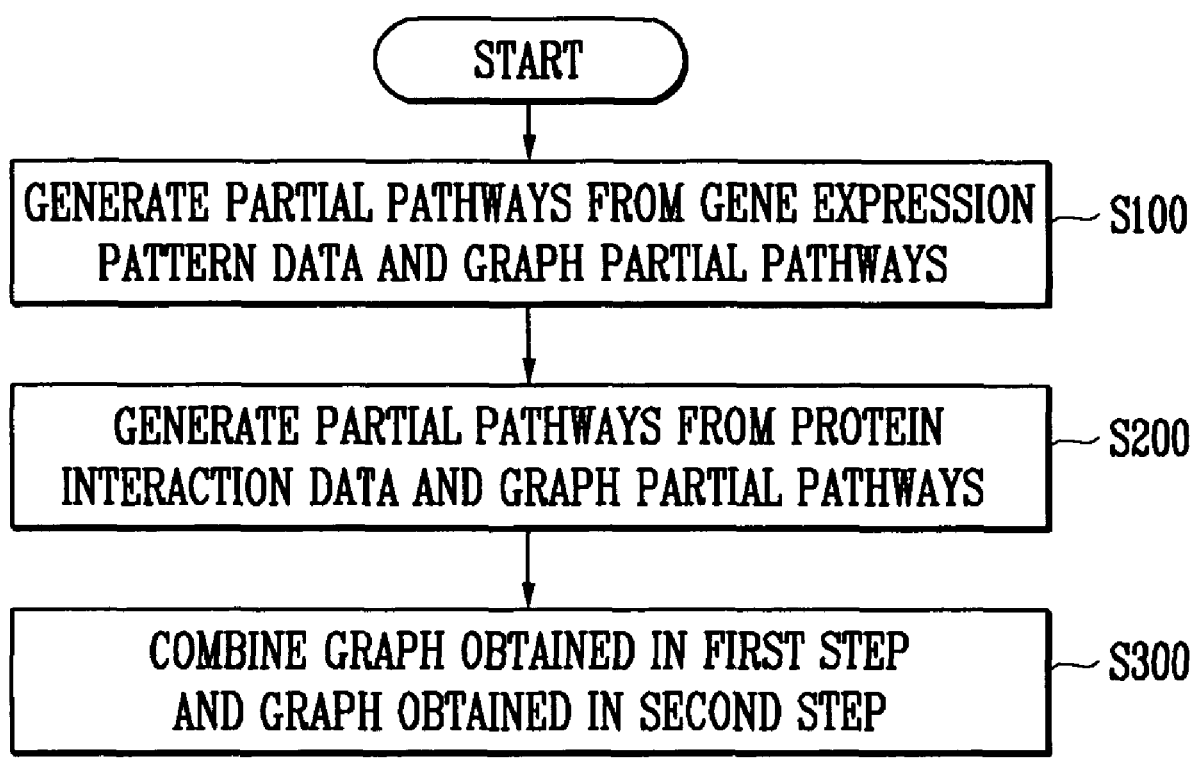
FIG. 1 is a flowchart illustrating a procedure for predicting a biological pathway of genes according to an exemplary embodiment of the present invention.
Figure 2:
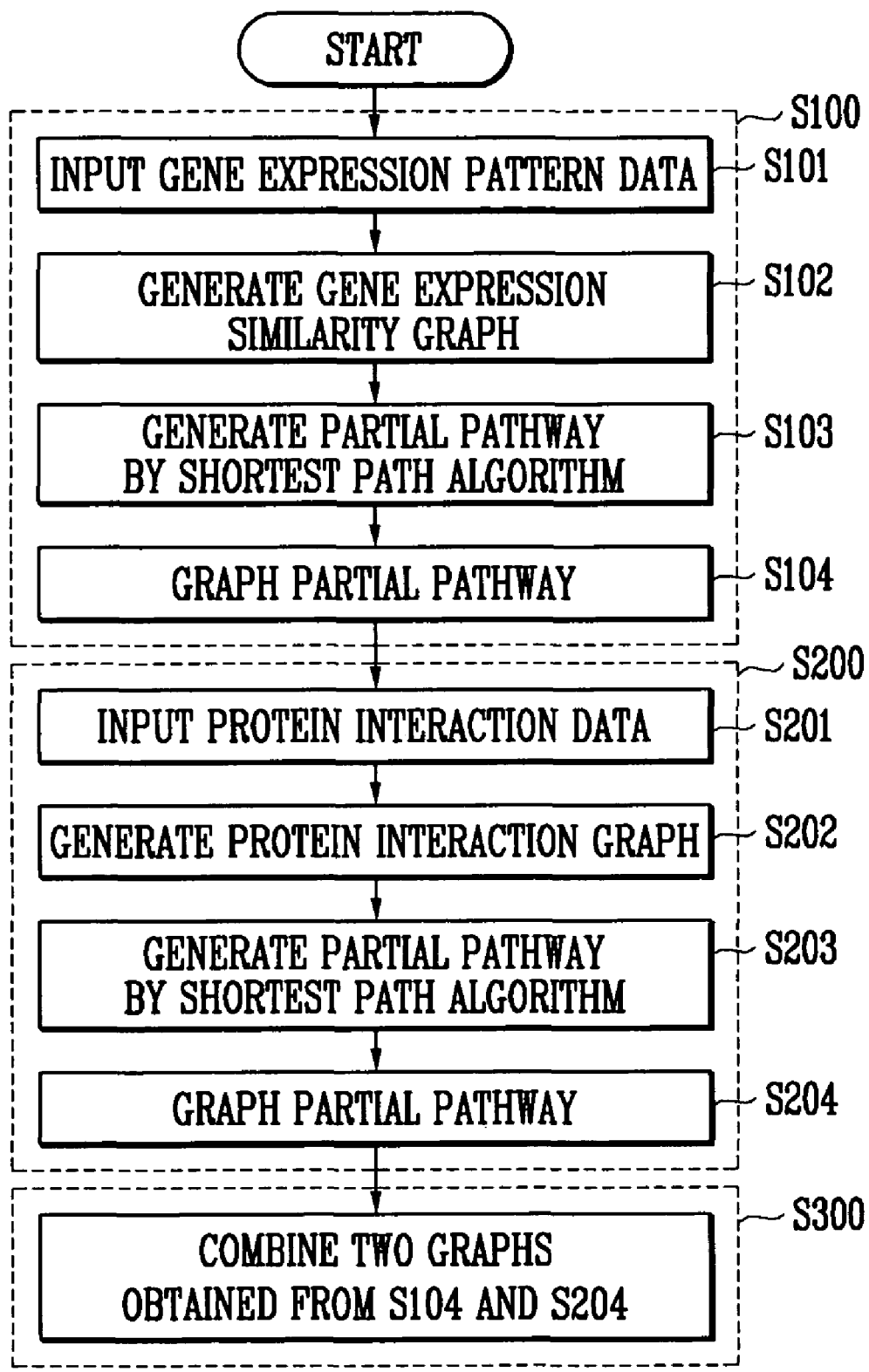
FIG. 2 is a flowchart illustrating a detailed procedure for predicting a biological pathway of genes according to an exemplary embodiment of the present invention.

FIG. 1 is a flowchart illustrating a procedure for predicting a biological pathway of genes according to an exemplary embodiment of the present invention, and FIG. 2 is a flowchart illustrating a detailed procedure for predicting a biological pathway of genes according to an exemplary embodiment of the present invention.

Referring to FIGS. 1 and 2, the method of predicting a biological pathway of genes according to the present invention comprises a first step S100 of generating partial pathways from gene expression pattern data using a pathway extraction algorithm, and matching the partial pathways to form a first graph, a second step S200 of generating partial pathways from PPI data using a pathway extraction algorithm, and matching the partial pathways to form a second graph; and a third step S300 of combining the first and second graphs using a graph matching algorithm to form a third graph.

The first step S100 comprises a step S101 of inputting the gene expression pattern data, a step S102 of generating a gene expression similarity graph from the gene expression pattern data by plotting each gene as a point, expressing gene expression pattern similarity as a distance between the points corresponding to the genes, and connecting the points if the distance between the two points is greater than a prescribed threshold, a step S103 of generating partial pathways from the gene expression similarity graph by the shortest path algorithm, and a step S104 of treating each of the generated partial pathways as a graph and combining them into a single graph using the graph matching algorithm.

The second step S200 comprises a step S201 of inputting the PPI data of genes, a step S202 of generating a PPI graph from the PPI data by plotting each gene as a point, expressing PPI similarity as distance between the points corresponding to the genes, and connecting the points if the distance between the two points is greater than is greater than a prescribed threshold, a step S203 of generating biological partial pathways from the PPI graph by the similar shortest path algorithm, and a step S204 of treating each of the generated partial pathways as a graph and combining them into a single graph using a graph matching algorithm. This procedure is described in *"Functional topology in a network of protein interactions"* by Natasa Przulj, Dennis A. Wigle, Igor Jurisica, Bioinformatics, volume 20, number 3, pages 340-348, 2004.

Finally, the graphs obtained from the first step S100 and the second step S200 are combined using a graph matching algorithm to produce a combined graph in the third step S300.

The method of predicting the biological pathway of genes according to the present invention will be explained in detail with reference to FIGS. 3 and 4.

(A) Generating Graph from Gene Expression Pattern Data

Figure 3:
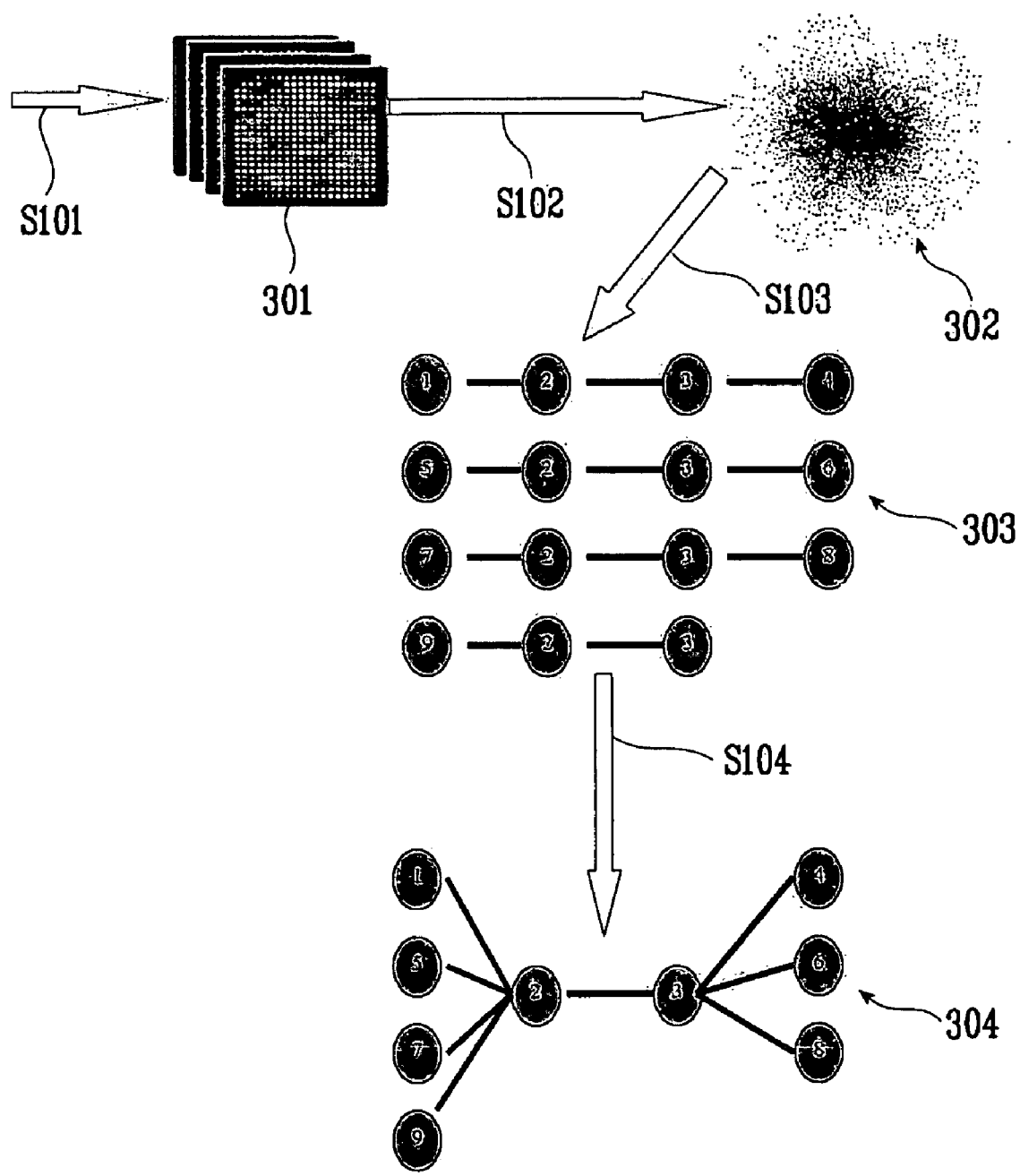
FIG. 3 is a diagram illustrating a method of generating partial pathways from the gene expression pattern data and expressing the partial pathways as a graph.

FIG. 3 is a diagram illustrating the first step of generating the partial pathways from the gene expression pattern data and expressing the partial pathways as a graph.

Referring to FIG. 3, gene expression pattern data 301 is input (S101). Here, the gene expression pattern data 301 is time-continuous mRNA expression pattern data generated by a DNA chip experiment, or an mRNA expression pattern data generated by an experiment such as reaction to a specific chemicals.

Such gene expression pattern data of each gene can be expressed by one mathematical vector. That is, if mRNA pattern data is obtained from n number of tests, the gene expression pattern data of each gene is expressed as an n-dimensional vector. Similarity between two genes expressed by the above-described method can be expressed by a mathematical distance between the genes using the vector. There may be many methods for measuring similarity but it may be preferably measured by a Euclidean distance metric.

Through the above-described distance measurement, a gene expression similarity graph 302 in which genes are plotted as points and a dstance between the points corresponding to the genes are measured is produced (S102). In the gene expression similarity graph 302, when an expression pattern similarity degree between genes is greater than the prescribed threshold, the corresponding points are connected. The threshold can be randomly selected, but preferably the points are connected when it is equal to or greater than 0.8 after vector normalization.

A path is calculated from the graph 302 by a module for calculating a path between two genes using the shortest path algorithm, and the path calculating procedure is performed for all gene pairs which act as a starting point and an ending point of a biological pathway to thereby generate every possible partial pathway 303 (S103).

A Dijkstra shortest path algorithm can be used as the module for calculating a path using the shortest path algorithm.

Here, as the genes which act as the starting point and the ending point, genes whose point degree in the expression similarity graph is lower than 4 are grouped. The partial pathways are generated for all possible pairs of genes, with one gene acting as the starting point S and the other acting as the ending point E, by using the shortest path algorithm.

Each of the partial pathways is considered as one graph, and when the number of points that are regarded as matched between two graphs is greater than a prescribed threshold, the graph matching algorithm which can determine a match is used to produce a graph 304 (S104). The threshold can be randomly selected but is preferably one half (½) of the total number of points.

(B) Generating Graph From Protein interaction data

The second step (S200) of generating partial pathways from PPI data of genes and graphing the partial pathways can proceed as described in *"Functional topology in a network of protein interactions"* by Natasa Przulj, Dennis A. Wigle, Igor Jurisica, Bioinformatics, volume 20, number 3, pages 340-348, 2004.

In more detail, the PPI data is input (S201). Here, the PPI data of each gene can be transformed into one mathematical vector and then expressed as a mathematical distance. Next, the PPI graph in which genes are plotted as points and connected by line segments is generated (S202). Here, if the PPI similarity degree between the genes according to the distance measurement method is greater than the prescribed threshold, the corresponding points are connected. Partial pathways are generated from the PPI graph by the shortest path algorithm, and all partial pathways are expressed by the graph structure (S204).

Here, the PPI data of the gene indicates which protein interacts with a corresponding protein of each gene. The forgoing data obtained by biological experiment is already stored in a database able to be used. To generate a partial pathway, genes whose point degree on the expression similarity graph are lower than 4 are used as the starting point and the ending point.

(C) Combining Gene Expression Pattern Graph and PPI Graph

Figure 4:
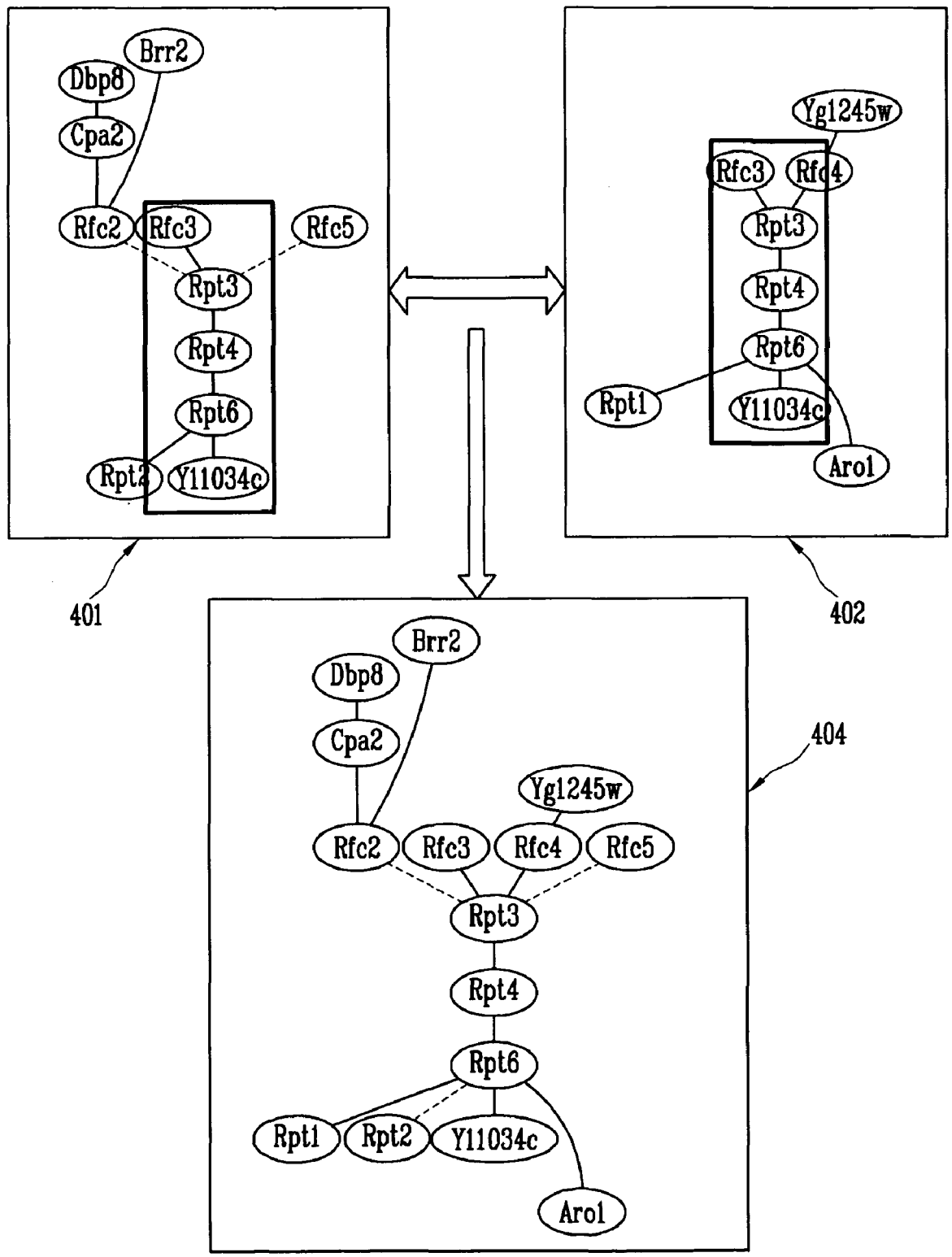
FIG. 4 is a diagram illustrating a method of coupling partial pathways obtained from gene expression pattern data and partial pathways obtained from PPI data according to the present invention.

FIG. 4 is a diagram illustrating a method of coupling the partial pathways obtained from the gene expression pattern data with the partial pathways obtained from the PPI data according to the present invention.

Referring to FIG. 4, information about the points that belong to the partial pathway 401 obtained from the gene expression pattern data and information about the points that belong to the partial pathway 402 obtained from the PPI data are investigated. There are points such as Brr2, Dbp8, Cpa2, Rfc2, Rfc3, Rpt3, Rpt4, Rpt6, Y11034c, Rpt2, and Rfc5 which belong to the partial pathway 401, and there are points such as Yg1245w, Rfc5, Rfc3, Rpt3, Rpt4, Rpt6, Y11034c, Rpt1, and Aro1 which belong to the partial pathway 402. Of these, the points which are contained in both gene groups are Rfc3, Rpt3, Rpt6, and Y11034c, as indicated by reference numeral 403. Since there are a sufficient number of points in both pathways, both pathways are subjected to a procedure for combining them into one, so that a pathway 404 is obtained. Here, there are a sufficient number of points in both pathways when the following condition is met:

$$S = \frac{|V401| \cap |V402|}{|V401| \cup |V402|} > \delta$$

where V401 denotes a group of points which belong to the pathway 401, V402 denotes a group of points which belong to the pathway 402, |V401| and |V402| denote the number of elements belonging to each group, and δ is input by a user.

Figure 5:
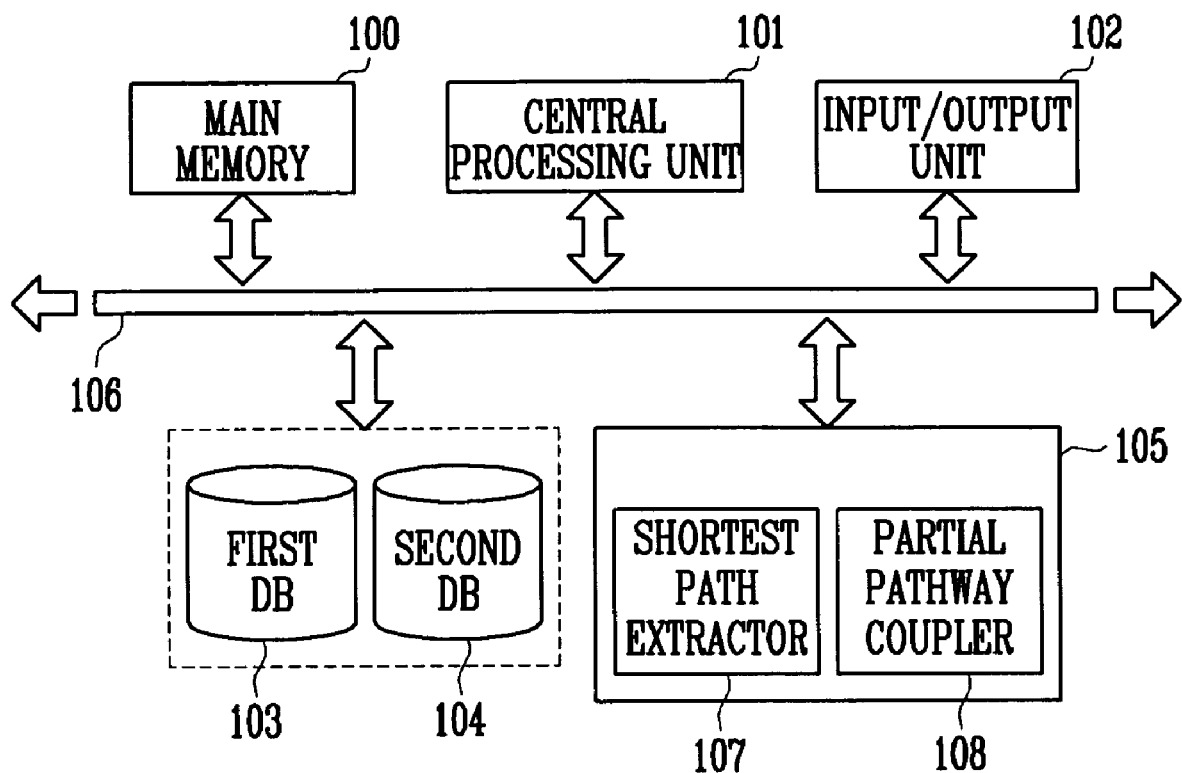
FIG. 5 is a block diagram of a system for predicting a biological pathway according to the present invention.

FIG. 5 is a block diagram illustrating a system for predicting a biological pathway according to an exemplary embodiment of the present invention. The system of FIG. 5 comprises a main memory 100, a central processing unit 101, an input/output unit 102, a first DB 103, a second DB 104, a pathway predicting unit 105, and a system bus 106. The pathway predicting unit 105 comprises a shortest path extractor 107 and a partial pathway coupler 108.

Referring to FIG. 5, the gene expression pattern data is input to build the first DB 103, and the PPI data is input to build the second DB 104. Here, the gene expression pattern data input to the first DB 103 is the time-continuous mRNA expression pattern data generated by the DNA chip experiment or the mRNA expression pattern data generated by an experiment such as reaction to prescribed chemicals. The PPI data input to build the second DB 104 indicates which protein interacts with a corresponding protein of each gene, and existing biological research data which were already built as a DB, can be used.

The main memory 100 stores the pathway predicting information and the information of the first DB 103 and the second DB 104, which are required in the respective steps.

The central processing unit 101 processes the pathway predicting information stored in the main memory 100 through the shortest path extractor 107 and the partial pathway coupler 108 of the pathway predicting unit 105 in the corresponding steps, and the input/output unit 102 receives information required in the system from a user and outputs the pathway predicting information automatically generated by the system on a screen. Messages or information are communicated between the respective components via a system bus 106.

As described above, the method of predicting the gene pathway according to the present invention simply analyzes the mRNA expression pattern of all genes and the PPI data of all possible proteins to search for gene pathways that serve the same biological purpose. The mechanism of disease development and gene pathways are predicted using the mRNA expression pattern data and the PPI data rather than by biological experiment, and thus time and cost can be saved and a highly reliable prediction result can be obtained using more than one type of biological data.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A computerized method of predicting a gene pathway using a computer, comprising:

a first step of generating partial pathways from gene expression pattern data by using a partial pathway extraction algorithm, and matching partial pathways to express said pathways as a graph;

a second step of generating partial pathways from Protein-Protein Interaction (PPI) data by using a pathway extraction algorithm, and matching the partial pathways to express said partial pathways as a graph;

a third step of combining the graph obtained in the first step and the graph obtained in the second step by using a graph matching algorithm to make a combined graph, the combined graph representing a predicted gene pathway, outputting the combined graph from the computer; and wherein the graph matching algorithm determines that the two graphs to be matched when the number of points regarded as identical between two graphs is greater than a prescribed threshold.

2. The method of claim 1, wherein the first step comprises the steps of:

inputting the gene expression pattern data;

generating a gene expression similarity graph from the gene expression pattern data by plotting each gene represented in said gene expression pattern data as a point, expressing gene expression pattern similarity as a distance between the points corresponding to the genes, and connecting the points if the distance between the two points is greater than a prescribed threshold;

generating the partial pathways from the gene expression similarity graph by using a shortest path algorithm; and expressing the partial pathways as a graph by using a graph matching algorithm.

3. The method of claim 1, wherein the second step comprises the steps of:

inputting the PPI data;

generating a PPI graph from the PPI data by plotting each gene represented in said PPI data as a point, expressing protein interaction similarity as a distance between the points corresponding to the genes, and connecting the points if the distance between the two points is greater than a prescribed threshold;

generating biological partial pathways from the PPI graph by using a shortest path algorithm; and expressing the partial pathways as a graph by using a graph matching algorithm.

4. The method of claim 2, wherein the gene expression pattern data is time-continuous mRNA expression pattern data obtained by a DNA chip experiment or an mRNA expression pattern data obtained by an experiment such as reaction to prescribed chemicals.

5. The method of claim 2, wherein when the gene expression pattern data is obtained by m-number of experiments, the gene expression pattern data is transformed into an m-dimensional vector, and expression similarity between genes is measured as a mathematical distance using the m-dimensional vector.

6. The method of claim 2, wherein genes whose point degree is lower than 4 are used as starting points and ending points, divided into two gene groups, and the shortest path algorithm is performed for all possible gene pairs between two gene groups.

* * * * *